(12) United States Patent
Horan et al.

(10) Patent No.: US 7,556,773 B2
(45) Date of Patent: *Jul. 7, 2009

(54) ANALYZER DEVICE AND METHOD

(75) Inventors: Martin Horan, Minane Bridge (IE);
Kathleen Horan, Drangan (IE); Seamus O'Mahony, Minane Bridge (IE)

(73) Assignee: Analytical Developments Limited, County Cork (IE)

( * ) Notice: Subject to any disclaimer, the term of this patent is extended or adjusted under 35 U.S.C. 154(b) by 37 days.

This patent is subject to a terminal disclaimer.

(21) Appl. No.: 11/847,421

(22) Filed: Aug. 30, 2007

(65) Prior Publication Data

US 2007/0292308 A1   Dec. 20, 2007

Related U.S. Application Data

(63) Continuation-in-part of application No. 11/235,176, filed on Sep. 27, 2005.

(51) Int. Cl.
*B01J 19/00* (2006.01)
(52) U.S. Cl. .............. 422/78; 422/68.1; 422/82.08; 422/82.09; 436/172
(58) Field of Classification Search ............. 422/68.1, 422/78, 82.05–82.09, 82.11, 236, 237; 436/145, 436/146, 160, 164–166, 172
See application file for complete search history.

(56) References Cited

U.S. PATENT DOCUMENTS 6,177,276 B1 * 1/2001 Richardson et al. ........... 436/55

6,623,974 B1   9/2003 Horan et al.

FOREIGN PATENT DOCUMENTS

| EP | 1039294 A2 | 9/2000 |
| JP | 08304376 A * | 11/1996 |
| WO | 94/07134 A1 | 3/1994 |

OTHER PUBLICATIONS

Kuo et al., Kinetics of Oxidation of Ammonia in Solutions Containing Ozone with or without Hydrogen Peroxide, Ind. Eng. Chem. Res. 1997, 36, 4108-4113.*
Machine translation of JP 08304376 A, Nov. 22, 1996, pp. 1-11.*

* cited by examiner

*Primary Examiner*—Jill Warden
*Assistant Examiner*—Shogo Sasaki
(74) *Attorney, Agent, or Firm*—Buskop Law Group, PC; Wendy Buskop

(57) ABSTRACT

An analyzer for oxidizing and measuring samples containing some liquid comprising: a reactor vessel; a sample pump; a base pump connected to a base reservoir; an ozone generator adapted to create and flow ozone; an acid pump connected to an acid reservoir; a sampling valve connected to the sample pump, the acid pump, and the base pump; a circulation pump connected to the reactor vessel for mixing the sample, the liquid acid, the liquid base, and the ozone to oxidize at least a portion of the sample to its lowest state forming an oxidized liquid sample; a sample chamber for receiving the oxidized liquid sample; an analysis pump in communication with the sample chamber; and a measuring cell for receiving the oxidized liquid sample, measuring the oxidized liquid sample with a detector to optically measure at least one frequency of absorption of at least one component in the sample.

17 Claims, 7 Drawing Sheets

ANALYZER DEVICE AND METHOD

CROSS REFERENCE TO RELATED APPLICATIONS

The present application is a continuation-in-part application which claims the benefit, under 35 USC §120, of the prior co-pending non-provisional application U.S. patent application Ser. No. 11/235,176 filed on Sep. 27, 2005.

FIELD

The present embodiments relate generally to an analyzer and a method for analyzing samples, including liquid samples.

BACKGROUND

The embodiments relate to a system for the analysis of one or more selected components in a liquid and particularly in aqueous solutions.

A need has existed to quickly and rapidly analyze samples in a continuous sampling device that has a flushing system capable of cleaning the sample lines between uses.

A need has existed for an automated device for continuously sampling liquid material or liquids containing some solids, including slurries and mixtures, oxidizing those samples, and determining the contents of those oxidized components.

The present embodiments meet these needs.

BRIEF DESCRIPTION OF THE DRAWINGS

The invention will be more clearly understood by the following description of some embodiments thereof, given by way of example only with reference to the accompanying drawings, in which.

Figure 1:
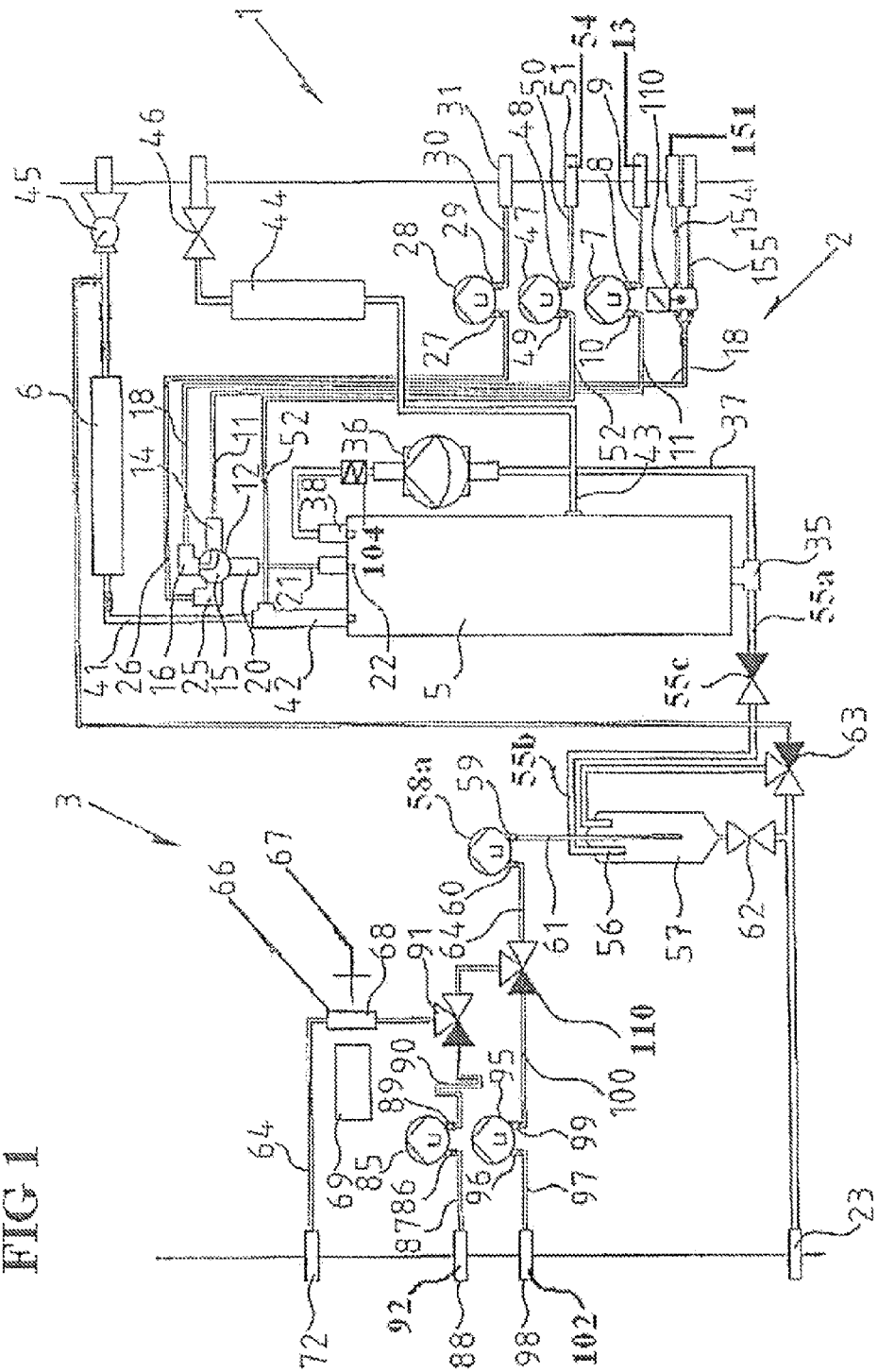
FIG. 1 is a schematic illustration of an embodiment of the analyzer.

The present embodiments are detailed below with reference to the listed Figures.

DETAILED DESCRIPTION OF THE EMBODIMENTS

Before explaining the present embodiments in detail, it is to be understood that the embodiments are not limited to the particular embodiments and that they can be practiced or carried out in various ways.

The present embodiments relate to an analyzer that is capable of rapid analysis of samples, including liquid samples, solutions, a sludge with solids, a liquid mixture, a slurry, an emulsification, other solutions and mixtures, or combinations thereof. The analyzer is capable of performing continuous sampling and possesses a flushing system, capable of cleaning the sample lines between uses, allowing numerous steps of the sampling and cleaning process to be performed simultaneously and continuously.

The present embodiments also allow for continuous sampling of a large variety of samples including liquids, liquids containing some solids, including slurries and mixtures, sludges, other similar samples, and combinations thereof. The present analyzer can oxidize these varied samples and determine the contents of those oxidized components.

In an embodiment, the analyzer has a reactor vessel for receiving a sample, which can be a liquid sample. A sample pump in communication with a sample source flows a sample into the reactor vessel. The sample source can contain a liquid, a solution, a sludge with solids, a liquid mixture, a slurry, an emulsification, other solutions and mixtures, or combinations thereof.

The analyzer further has a base pump connected to a base reservoir or other base source for flowing a liquid base, such as 1.2N sodium hydroxide, to the reactor vessel. An ozone generator in communication with the reactor vessel creates ozone, either from an oxygen source or liquid source and flows ozone to the reactor vessel. The analyzer has an acid pump connected to an acid reservoir, or other acid source, for flowing a liquid acid, such as 1.8N sulphuric acid, to the reactor vessel. The acid reservoir and base reservoir can include any source of liquid acid or liquid base, respectively, including the manual or automated addition of liquid acid or liquid base, or the electrochemical generation of liquid acid and liquid base, such as by membrane technology and a salt source.

All the liquid base, liquid acid, and ozone can be regulated with valves, which can be one-way valves, two-way valves, or three-way valves. The valves can be manually controlled or automatically controlled, such as through using sensors connected to a processor for monitoring flow rates into the reactor vessel for any given sample.

The processor can be an integrated processor within the analyzer or it can be an external computer.

The processor can be directly controlled by a user at a display or it can be connected to network, such as the internet, and remotely monitored by a user using a client device in communication with the processor through one or more gateway protocols. The client device can be a cellular phone, a personal digital assistant, or a similar device.

Further, in a contemplated embodiment, the processor can be electrically connected to all components in the analyzer, controlling all valves, pumps, and other components of the analyzer. The processor can also be used to read the resulting data, to perform calculations, and to display results. Any number of results relating to any amount of data can be displayed on one or more display, such as computer monitors, printed reports, or a remote display such as a cellular telephone, a personal digital assistant, or a similar device, and combinations thereof.

It is contemplated that the processor can be used to calculate Chemical Oxygen Demand (COD) by the application of an algorithm to one or more of the measured components, such as total carbon, organic carbon, inorganic carbon, nitrogen, phosphorous, nitrate, phosphate, ammonia, others, and combinations thereof. This calculation and others can be carried out by an integrated processor or by an external computer.

The use of a processor in this embodiment allows the operation of the analyzer to be fully automated.

In an embodiment, a sampling valve is connected to the flows from the sample pump, the acid pump, and the base pump. The sampling valve is used to selectively flow the sample, the liquid base, and the liquid acid simultaneously, or sequentially, or in pairs, or other combinations thereof, into the reactor vessel. The sampling valve can have an internal flow controller.

In the embodiment, the analyzer includes a circulation pump connected to the reactor vessel for mixing the sample, the liquid acid, the liquid base, and ozone to generate hydroxyl radicals for oxidizing at least a portion of the sample to its lowest state in solution, forming oxidized material, which is also referred to as the oxidized liquid sample.

The embodiment of the analyzer further includes a sample chamber in communication with the reactor vessel. The sample chamber receives the oxidized liquid sample.

An analysis pump is in communication with the sample chamber. The analysis pump pulls fluid from the reactor vessel through a measuring cell for detecting oxidized components by at least a first detector. More than one detector can be within the measuring cell.

In another embodiment, the measuring cell can be translucent.

The measuring cell is connected to the analysis pump and the sample chamber. It should be noted that if two or more detectors are used, such as three, four, five, or even eight detectors, each detector can be used for determining different frequencies of absorption for the components in the oxidized liquid sample. The detectors can be used to optically measure for different frequencies of absorption of nitrogen, phosphorus, heavy metals, copper, aluminum, carbon, and other similar metals and materials.

It is contemplated that another type of detector can be used, that of at least one ammonia gas detector connected to the reactor vessel. Additionally, in this embodiment using the ammonia gas detector, it is contemplated that an ammonia gas removal device can be connected to the reactor vessel for removing ammonia gas from the reactor vessel. The ammonia gas removal device can be a pump.

A cleaning pump is used in yet another embodiment of the invention. In this embodiment, the cleaning pump is connected to a cleaning fluid reservoir. The cleaning pump pulls cleaning fluid from the cleaning fluid reservoir to clean the measuring cell between sample measurements. A typical cleaning solution could be 1.8N hydrochloric acid in water.

The cleaning pump can be part of a cleaning system for cleaning the entire sample delivery system of the analyzer. For the purpose of this embodiment, the sample delivery system is defined as the sample pump with a sample delivery line having a sampling valve for moving sample from a sample source into the sample chamber.

In another embodiment, a flushing pump can be used, with or without the cleaning pump, to clean the analyzer. When a flushing pump is used, the flushing pump pulls water from a water supply to flow through the measuring cell.

In still another embodiment, a reagent pump can be used. The reagent pump can be connected to a reagent source for supplying a reagent to the oxidized liquid sample for calorimetric measurement of the oxidized liquid sample.

In yet a different embodiment, it is contemplated that a flow controller can be disposed between the ozone generator and an oxygen source to create controlled ozone production.

An embodiment additionally contemplates having an ozone destructor in communication with the reactor vessel. The embodiment can also include a carbon dioxide analyzer in the analyzer, or combinations of the ozone destructor and the carbon dioxide analyzer.

The carbon dioxide analyzer, like the ozone destructor, can be connected to the reactor vessel for detecting, measuring, or detecting and measuring inorganic carbon, organic carbon, sodium oxalates, or combinations of these components. In addition to the carbon dioxide analyzer, the analyzer can include a carbon dioxide removal device for removing carbon dioxide or carbonate from the reactor vessel. The carbon dioxide removal device can be a pump.

The analyzer can have a two-way acid control valve with an inlet for the liquid acid from the acid pump, a first outlet for the liquid acid to the sampling valve, and a second outlet for the liquid acid to the reactor for supplying these components to the reactor vessel.

The analyzer can also have a two-way base control valve with an inlet for the liquid base from the base pump, a first outlet for the liquid base to the sampling valve, and a second outlet for the liquid base to the reactor vessel.

A catalyst can be used in the reactor of the analyzer to facilitate oxidation of the sample, sample recovery, or combinations thereof. The catalyst can be a metal catalyst, such as a catalyst having at least a portion that is manganese, nickel-silver, another nickel halide, or a similar catalyst for reducing oxylates to carbonates.

An embodiment contemplates that there can be a power connection enabling the analyzer to run pumps and valves for continuous operation of the analyzer.

The analyzer is contemplated to have a plurality of measuring cells and detectors for measuring different properties of the oxidized sample. At least one of the detectors can be an optical detector. The detector or detectors can be used to determine nitrogen concentration, phosphorous concentration, ammonia concentration, concentrations of heavy metal, copper, aluminum, other similar metals, or combinations of these components. In one embodiment of the analyzer, the detector could be a photodiode array for optically measuring at least one component of the oxidized liquid sample.

Referring now to FIG. 1, there is illustrated an analyzer 1. The analyzer 1 has a reactor portion 2 and a measuring portion 3. In the reactor portion 2 is a reactor vessel 5. In the embodiment of FIG. 1, the measuring portion 3 measures the total nitrogen content of a sampled liquid. Other components can also be measured in the measuring portion.

A sample pump 7 has a pump inlet 8 connected by a pump inlet line 9 to a sample source for removing a sample to be tested. The sample pump has a pump outlet 10 connected to a sample delivery line 11 with a sampling valve 12 for delivering a liquid sample 13 from the sample source to a first sampling valve inlet 14 of the sampling valve 12.

The sampling valve 12 can have an internal flow controller 15 which controls the flow of liquid through the sampling valve 12.

Figure 6A:
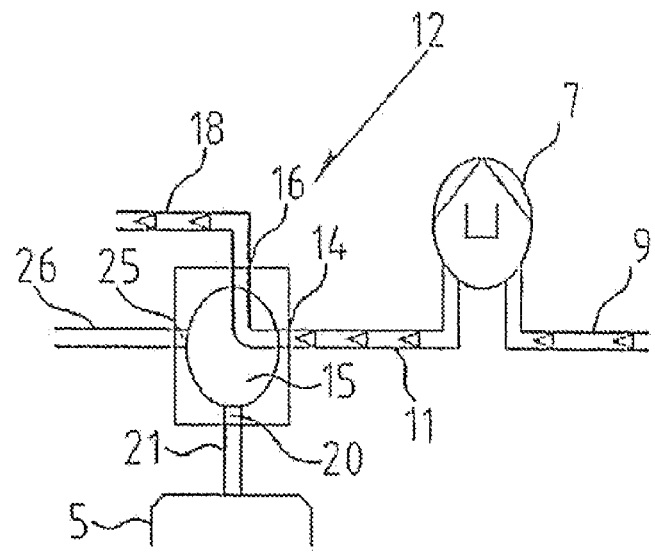
FIG. 6 is a schematic illustration of a sampling valve portion of the analyzer in different modes of operation.

Operation of this internal flow controller 15 is shown in FIG. 6. In FIG. 6a, the flow controller is depicted connecting the first sampling valve inlet 14 using a bypass outlet 16. The bypass outlet 16 connects to a bypass line 18. In this configuration, a liquid sample 13 is delivered by the sample pump 7 to the bypass line 18.

Figure 6B:
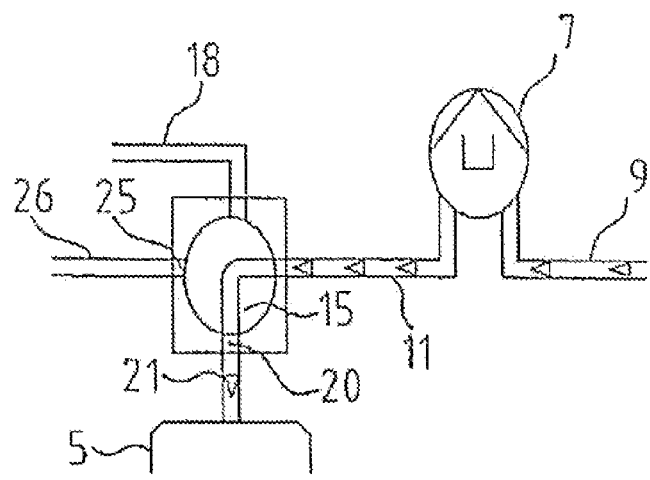

FIG. 6b shows the internal flow controller 15 rotated approximately 90 degrees to connect the first sampling valve inlet 14 with a sampling valve reactor outlet 20 which communicates through a transfer pipe 21 with a sample inlet 22 of the reactor vessel 5. In this configuration, a liquid sample 13 is delivered by the sample pump 7 to the reactor vessel 5.

Figure 6C:
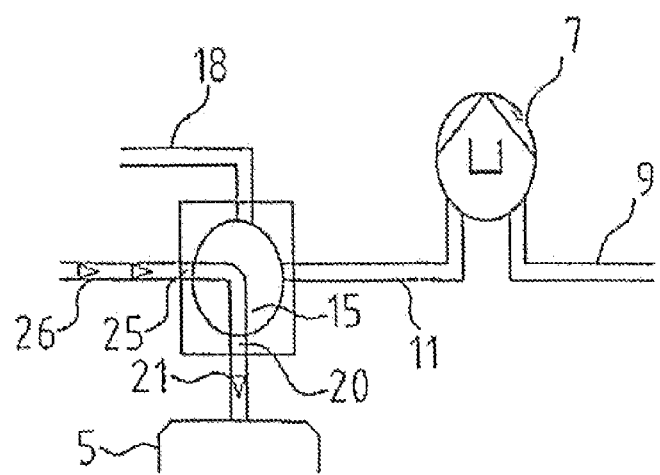

FIG. 6c shows the internal flow controller 15 further rotated approximately 90 degrees to connect the sampling valve reactor outlet 20 with a base inlet 25. The base inlet 25 connects to a base inlet line 26 leading from a base outlet 27 of a base pump 28. A base pump inlet 29 of the base pump 28 connects via a base pump inlet line 30 to a base reservoir 31 containing liquid base 4.

Returning to FIG. 1, the reactor vessel 5 has a reactor vessel outlet 35. A circulation pump 36 is mounted in a pipe 37 connected between the reactor vessel outlet 35 and a recirculation inlet 38 of the reactor vessel 5. In an embodiment a UV oxidizing chamber 104 is between circulation pump 36 and reactor 5. UV oxidizing chamber 104 can incorporate a UV lamp light source, such as a light source manufactured by Heraevs of Germany, having a helically coil lamp or straight lamp. Pump 36 can be used for flowing oxidized material around the lamp. Fluid flows from pump 36 to the UV oxidation chamber 104 and back to reactor 5. The UV oxidizing chamber assists in the breakdown of chlorinated compounds and other halogenated and non-halogenated compounds. It is contemplated that using a combination of reactions with or without additional UV oxidation, chlorinated compounds and other halogenated compounds can be measured.

An ozone generator 6 has an ozone generator outlet line 41 leading to an ozone inlet 42 of the reactor vessel 5. An ozone outlet pipe 43 leads from the reactor vessel 5 through an ozone destructor 44 and exhaust valve 46 to exhaust from the analyzer 1.

An acid pump 47 has an acid pump inlet 48 and an acid pump outlet 49. The acid pump inlet 48 connects through acid inlet pipe 50 with an acid reservoir 51. The acid pump outlet 49 connects through acid delivery line 52 with the reactor vessel 5. In an embodiment, a catalyst 39 can be combined with liquid acid 54 pulled by the acid pump from the acid reservoir.

The reactor vessel outlet 35 also connects through a discharge line 55a with an inlet pipe 55b to a sample chamber 57. A stop valve 55c can be mounted in the discharge line between pipes 55a and 55b.

An analysis pump 58a has an analysis pump inlet 59 and an analysis pump outlet 60. The analysis pump inlet 59 connects through a suction line 61 with the sample chamber 57. The analysis pump outlet 60 connects through a delivery line 64 which further has a first detector 66. The first detector 66 has a light source 67 for directing light through a measurement cell 68, which can be translucent, and is located in the delivery line 64. More than one measurement cell can be used.

Light transmitted by the light source 67 through the measurement cell 68 is then sensed by a second detector 69 located at an end of the measurement cell 68 opposite the first detector. Downstream of the measurement cell 68 the delivery line 64 leads to a drain 72.

A cleaning pump 85 has a cleaning pump inlet 86 connected by a cleaning fluid suction pipe 87 to a cleaning fluid reservoir 88 for retrieving cleaning fluid 92 from the cleaning fluid reservoir 88. A cleaning fluid outlet 89 of the cleaning pump 85 connects through a cleaning fluid supply line 90 and a cleaning fluid three-way valve 91 with the delivery line 64.

A flushing pump 95 has a flushing pump inlet 96 connected by a water suction pipe 97 to a water supply 98. A flushing pump outlet 99 of the flushing pump 95 connects through water delivery line 100 with a flushing valve 101 in the delivery line 64. Water 102 can be in the water supply 98 for flushing.

In operation, the sample pump 7 is operated to deliver a liquid sample 13 through the sampling valve 12 and out through the bypass line 18. During this operation, the internal flow controller 15 is in the position shown in FIG. 6a.

When a fresh liquid sample 13 is at the sampling valve 12, the flow controller 15 rotates clockwise by 90 degrees to the position shown in FIG. 6b, and a measured quantity of liquid sample 13 is pumped into the reactor vessel 5 by the sample pump 7. Typical sample volumes are up to 10 ml and may as small as 0.4 ml or smaller depending on the range to be measured.

The flow controller 15 of the sampling valve 12 can be rotated clockwise by a further 90 degrees into the position shown in FIG. 6c. In this position, the sample remaining in the transfer pipe 21 is flushed by liquid base delivered from the base pump 28 through the sampling valve 12. This also raises the pH in the reactor vessel 5 to greater than pH 12 and preferably to about pH 14.

Then, the circulation pump 36 is operated, the ozone generator 6 is switched on, and an oxygen flow control device, flow controller 45 passes a measured flow of oxygen gas into the ozone generator 6 and then ozone 17 into the reactor vessel 5. The sample is oxidized in the reactor vessel 5 using hydroxyl radicals, forming oxidized liquid sample 40.

At the same time, the flow controller 15 in the sampling valve 12 is rotated 180 degrees, returning to its start position, which is shown in FIG. 6a. The sample pump 7 is run in reverse, emptying the sample line 11. Conveniently, at the same time the spent fluid is discharged through the drain outlet 23, a cleaning valve 110 mounted in the bypass line 18 can be activated while the sample pump 7 is running in reverse, and this acidic material is then used to wash the sample line 11 and keep it clean, without the use of additional chemicals. This can be seen more clearly in FIG. 5.

When oxidation is complete, the acid pump 47 is operated, and the pH in the reactor vessel 5 is reduced to below pH 1. Any carbon dioxide in the liquid is sparged off by the flow of oxygen.

The acid can also contain a small amount of catalyst, for example manganese. This is used as a catalyst in the reaction, and it is desirable as it converts oxalate to carbon dioxide gas. The purpose of the catalyst is to eliminate interference from oxalate and to support 100% recovery of all carbon. By using a combination of acids with and without a catalyst, this technique can be extended to include measurement of oxalates in the sample.

When all the carbon dioxide has been released, a stop valve 55c downstream of the reactor vessel outlet 35 opens, the exhaust valve 46 closes, and liquid in the reactor vessel 5 is dumped to the sample chamber 57. A drain valve 62 of the sample chamber 57 is closed so that the liquid remains trapped in the sample chamber 57.

At this point nitrogen analysis of the liquid in the sample chamber 57 starts.

However, to save time, during the analysis, the oxidation process as described previously can repeat to prepare a new sample liquid for testing. Prior to reception of the sample liquid in the sample chamber 57, the measuring portion 3 will be made ready for analysis by filling the measuring cell 68 with clean water 102 delivered through the delivery line 64 by the flushing pump 95, which can be a water pump, and then a blank spectrum is obtained for the clean water sample.

The analysis pump 58a is run until the measuring cell 68 is full of oxidized sample delivered from the sample chamber 57 by the analysis pump 58a. The light source 67 switches on. The light source 67 can conveniently be provided by a deuterium lamp, which gives a good spectral output from below 200 nm to above 400 nm. Other light sources may be used for measurement in different spectral areas.

The spectrum is measured using the detector 69, which can have a photodiode array. A primary measuring frequency can be 217 nm, and other frequencies can be used for comparison. This spectrum is compared with the blank spectrum, obtained for the clean water as mentioned above, and the measurement is calculated to give a measurement of total nitrogen content in the sample.

The nitrogen measuring system is then cleaned. The analysis pump 58a runs in reverse, emptying the delivery line 64. The drain valve 62 opens, a purge valve 63 changes state so that a flow of oxygen gas from the flow controller 45 forces liquid in the sample chamber 57 through the drain valve 62 and out to drain outlet 23.

The cleaning fluid three-way valve 91 changes state, and the cleaning pump 85 is run for about two seconds, flushing the measuring cell 68 with a cleaning fluid. A typical cleaning solution will be HC1 in water approximately 1.8N. This cleaning fluid remains in the measurement cell 68 for about one minute. The cleaning pump 85 can then be run for two seconds and then in reverse for two seconds. This has the effect of pushing the contaminated cleaning fluid down the drain 72 and at the same time recovering the cleaning fluid used to flush the contaminated cleaning fluid from the measuring cell 68. When the cleaning pump 85 has run in reverse for approximately two seconds, the measurement cell 68 and lines from the cleaning valve 91 to the drain should be empty.

The flushing valve 101 is then opened, and the flushing pump 95 is run for about twenty seconds, flowing flushing water through the delivery line 64, washing any traces of cleaning fluid from the measurement cell 68 and filling the measurement cell 68 with clean water ready for measuring the blank spectrum as described previously. This process described above is then repeated at timed intervals as required.

Figure 2:
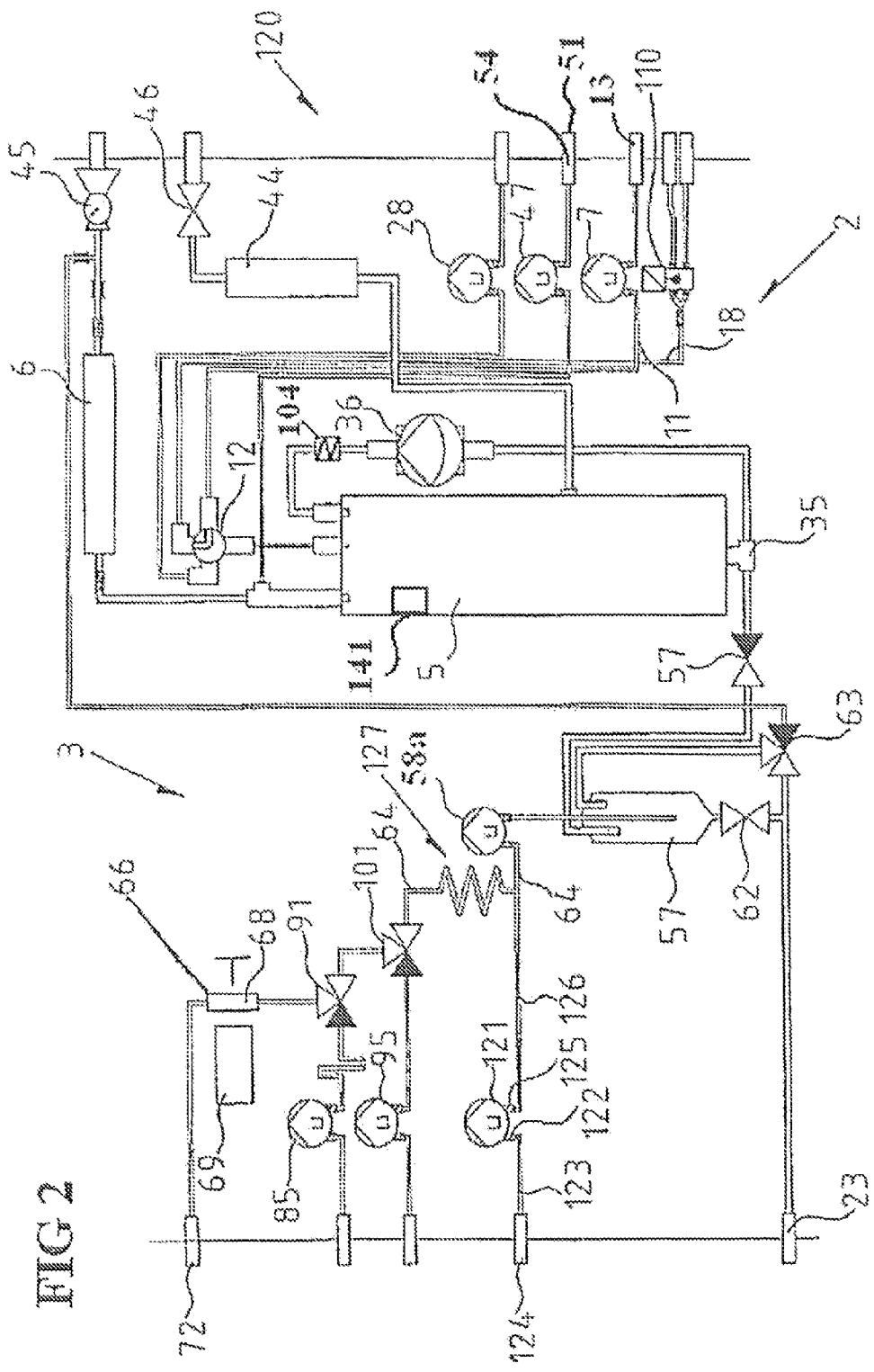
FIG. 2 is a schematic illustration of another embodiment of the analyzer.

Referring now to FIG. 2, there is shown another analyzer according to a second embodiment of the invention, indicated generally by the reference numeral 120. This is largely similar to the analyzer described previously with reference to FIG. 1, and like parts are assigned the same reference numerals. The measurement portion 3 of the analyzer 120 in this case further includes a reagent pump 121 having a reagent pump inlet 122 connected by a reagent pump suction pipe 123 with a reagent reservoir 124. A reagent pump outlet 125 of the reagent pipe 121 discharges through reagent pipe 126 into the delivery line 64. A mixer 127 which optionally includes a heater or a hydrolyzing unit is provided in the delivery line 64 for mixing reagent with the sample liquid discharged from the analysis pump 58a prior to delivery of the mixture to detector 66.

In operation, the sample 13 is prepared in the reactor vessel 5 and delivered to the sample chamber 57 in the same way as was described previously for the analyzer of FIG. 1. For nitrogen analysis, the analysis pump 58a runs, and after a short delay of about three seconds, the reagent pump 121 runs. The fluids discharged from the analysis pump 58a and the reagent pump 121 mix in the mixer 127, which can be a mixing tube.

When mixed, the mixture is pumped into the measuring cell 68 and measured, typically at a single wavelength. Both nitrogen and phosphate can be measured at 400 nm. Other components can also be measured at other wavelengths. The measurement is calculated from this reading and the blank spectrum. The measurement portion 3 is cleaned in the same way as described previously for the analyzer of FIG. 1. The process is repeated at timed intervals.

Figure 3:
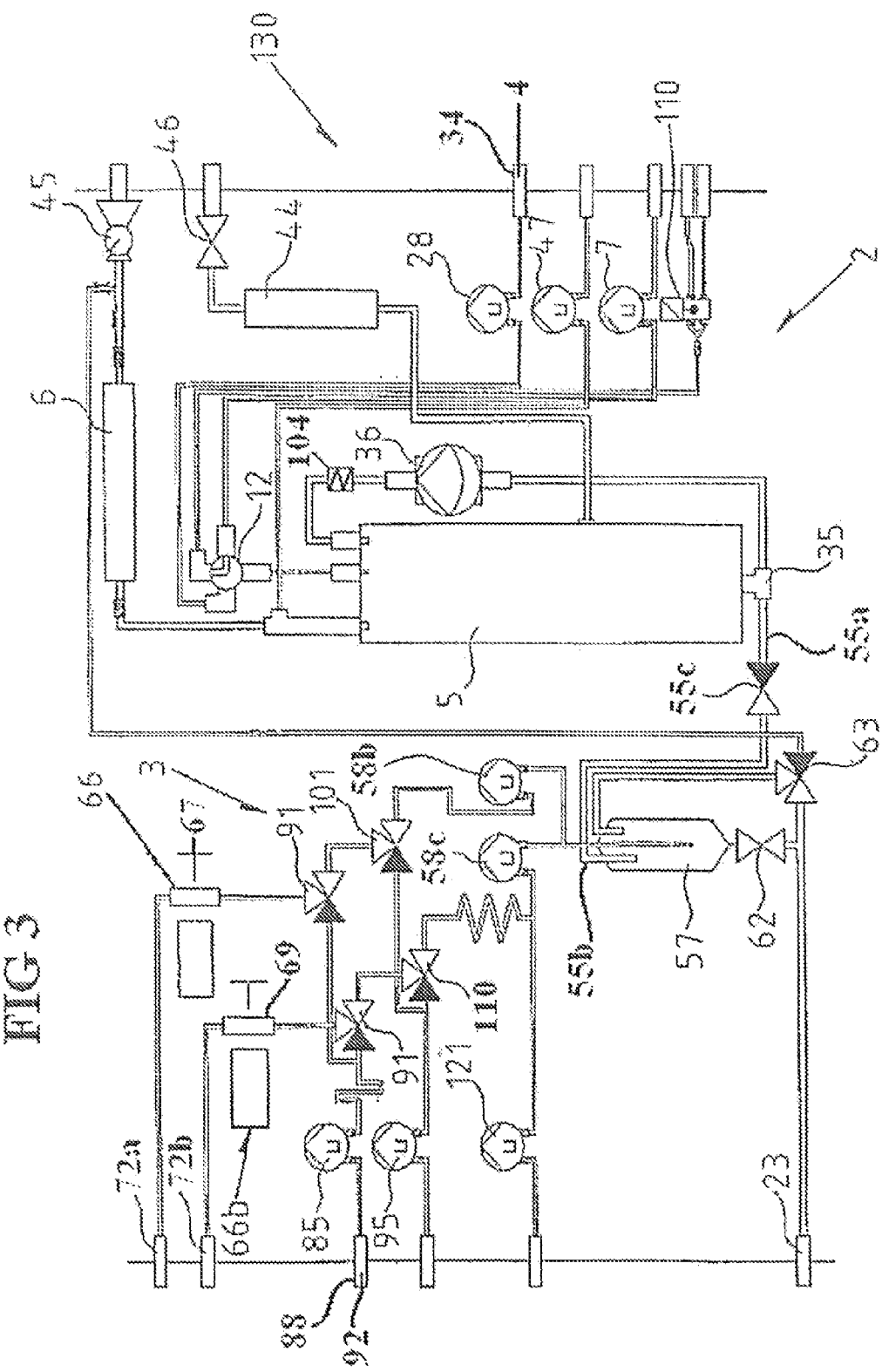
FIG. 3 is a schematic illustration of a third embodiment of the analyzer.

Referring to FIG. 3, there is shown another analyzer according to a third embodiment of the invention indicated, generally by the reference numeral 130. This analyzer 130 is largely similar to the analyzers described previously in FIG. 1 and FIG. 2, and like parts are assigned the same reference numerals. In this embodiment, the measurement portions 3 of the analyzers shown in FIGS. 1 and 2 have essentially been combined, and the operation is largely similar. However, a separate nitrogen analyzer pump 58b and a phosphate analyzer pump 58c are provided for delivery of liquid from the sample chamber 57 through a nitrogen detector 66 and a phosphate detector 69.

Figure 4:
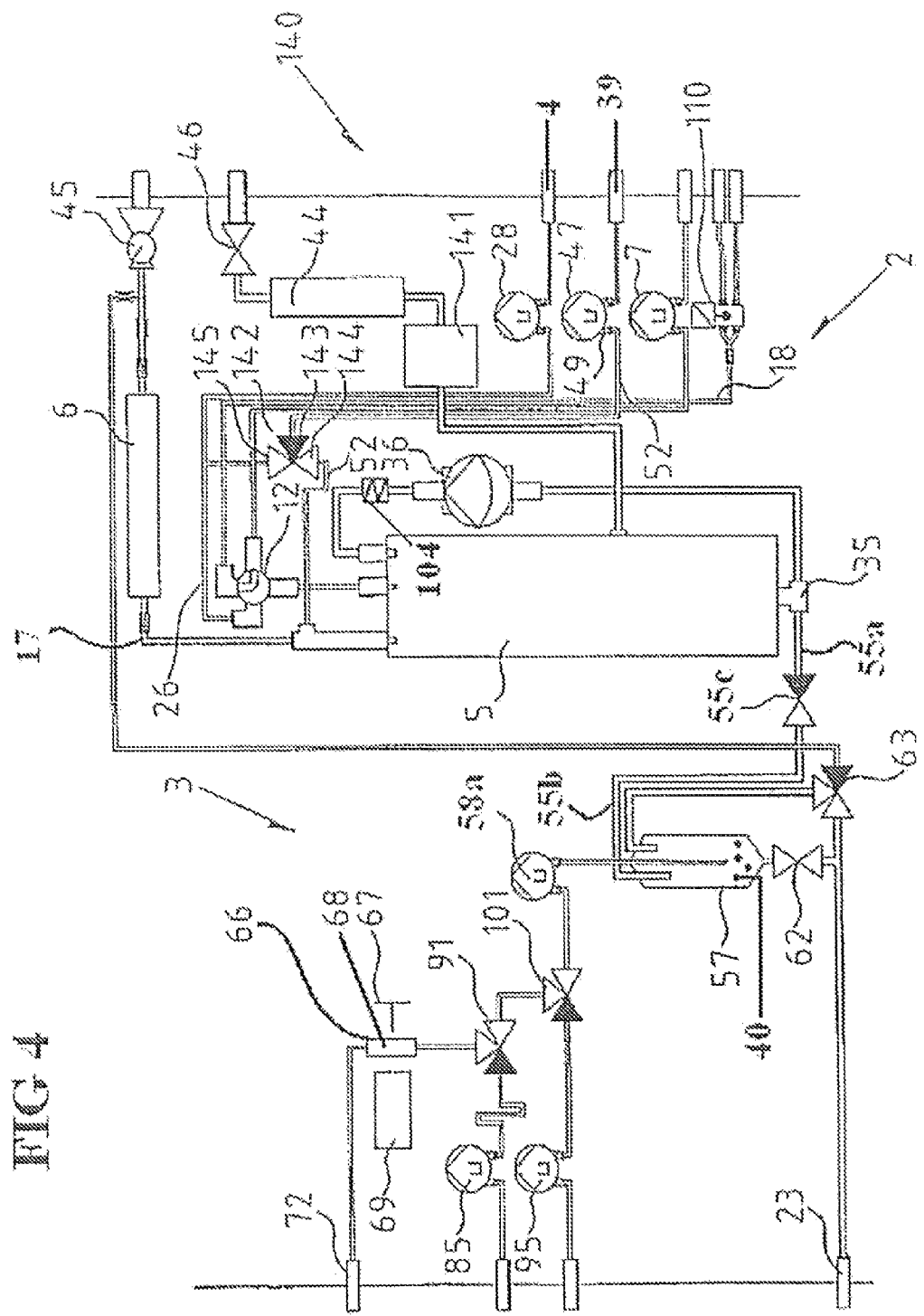
FIG. 4 is a schematic illustration of a fourth embodiment of the analyzer.

FIG. 4 shows another analyzer according to a fourth embodiment of the invention, indicated generally by the reference numeral 140. Parts similar to those described previously in FIG. 1, FIG. 2, and FIG. 3 are assigned the same reference numerals. Analyzer 140 is essentially the same as the analyzer shown in FIG. 1, except in this embodiment, a carbon dioxide analyzer 141 is mounted in the ozone outlet pipe 43, between the reactor vessel 5 and the ozone destructor 44.

Analyzers, such as infra red analyzers, to analyze other materials could be inserted here also. The carbon dioxide analyzer 141 measures the carbon dioxide gas released from the oxidized solution in the reactor vessel 5 when the pH is reduced to less than seven. With an appropriate calibration, the gas measurement can be converted to total carbon, or total organic carbon if the total inorganic carbon is known. The carbon dioxide analyzer 141, or another analyzer, could similarly be inserted in any of the analyzers shown in FIGS. 1, 2, 3, and 5 if desired.

An at least two-way acid control valve can be used in the acid delivery line. This embodiment shows a three-way acid control valve 142 provided in the acid delivery line 52. This acid control valve 142 has an inlet 143 for acid from the acid pump 47 connected to the acid pump outlet 49, a first outlet for the acid 144 connected to the reactor vessel 5, and a second outlet for the acid to the sampling valve 145 for delivery of acid to the sampling valve 12.

Normally, the second outlet for the acid to the sample valve 145 will be shut and the first outlet for the acid 144 will be opened. This configuration corresponds to the configuration shown in FIG. 1. The two-way, or as depicted in FIG. 4, the three-way acid control valve 142 can be switched to shut the first outlet for the acid 144 connected to the reactor vessel and then open the second outlet for the acid to the sampling valve 145. This process allows acid to be delivered to the reactor vessel 5 with the liquid sample initially to lower the pH. Carbon dioxide formed can be stripped off to measure total inorganic carbon present in the sample prior to switching back the three-way acid control valve 142 and adding the liquid base 4 to the reactor vessel 5.

Figure 5:
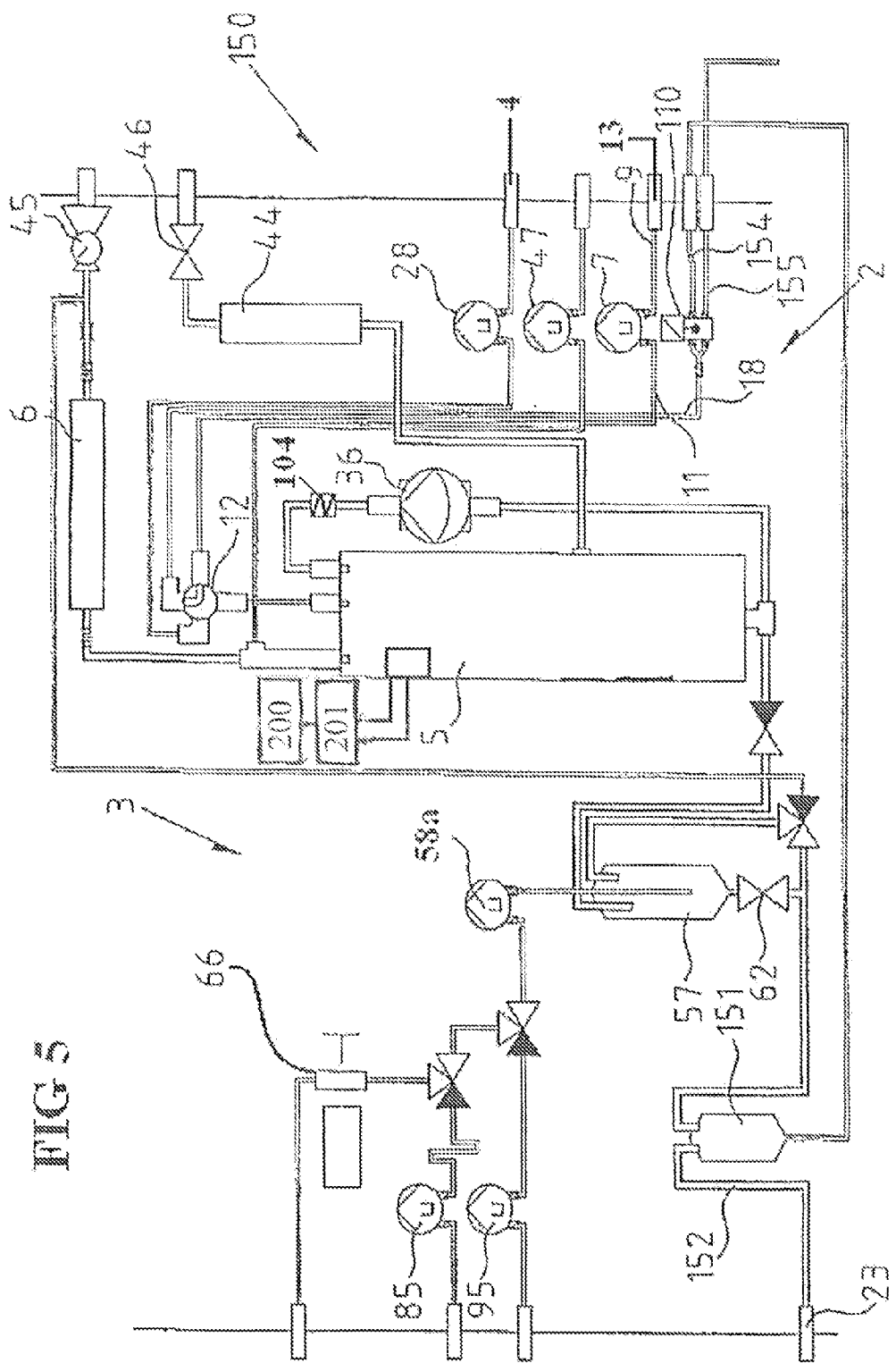
FIG. 5 is schematic illustration of a fifth embodiment of the analyzer.

Referring now to FIG. 5, there is shown another analyzer according to a fifth embodiment of the invention, indicated generally by the reference numeral 150. Parts similar to those described previously are assigned the same reference numerals. This embodiment is largely similar to the analyzer shown in FIG. 1, however in this embodiment, provision is provided for cleaning the sample delivery line 11 by collecting the spent chemicals, the oxidized liquid sample from the reactor vessel 5.

These oxidized portions are collected in a vessel 151 which has a safety overflow 152 to a drain 23. When the sample pump 7 runs in reverse and the cleaning valve 110 is switched so that an upper line 154 is opened and the lower bypass drain line 155 is closed, the spent chemicals are brought from the vessel 151 and drawn through the sample valve 12 into the sample line 11, through the sample pump 7, and out through the pump inlet line 9 to clean the sample loop.

The reactor vessel 5 of FIG. 5 also has an ammonia gas detector 200, such as a MimiMax XP Ammonia Single Gas Detector (Item # G507-6766 manufactured by Honeywell/Zellweger Analytics/Lumidor). Other similar detectors can also be connected to the reactor vessel 5. Reactor vessel 5 can also have a gas removal device 201, such as a pump, for removing ammonia or other gasses from the reactor vessel 5 for measurement.

FIG. 7 shows operation of the sampling valve 12 for use with very small samples.

Figure 7A:
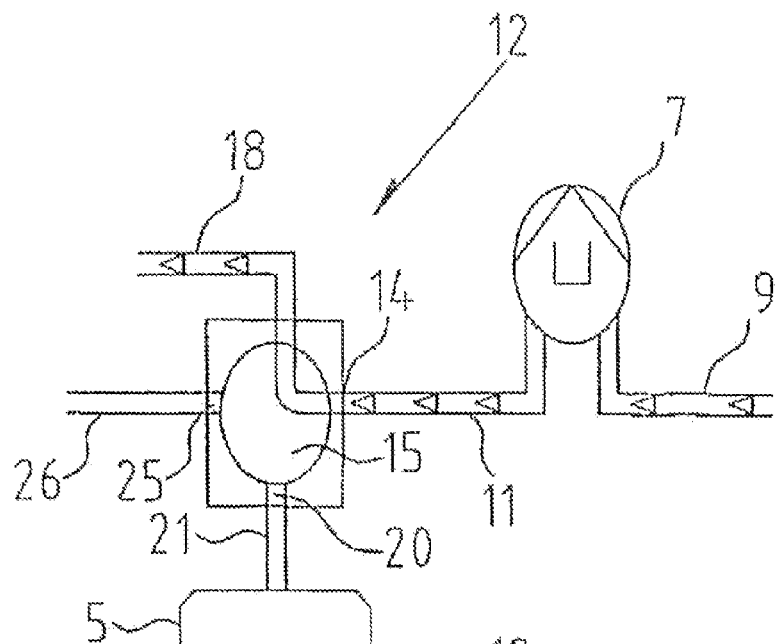
FIG. 7 depicts schematic views showing the sampling valve portion of the analyzer in yet another mode of operation.
Figure 7B:
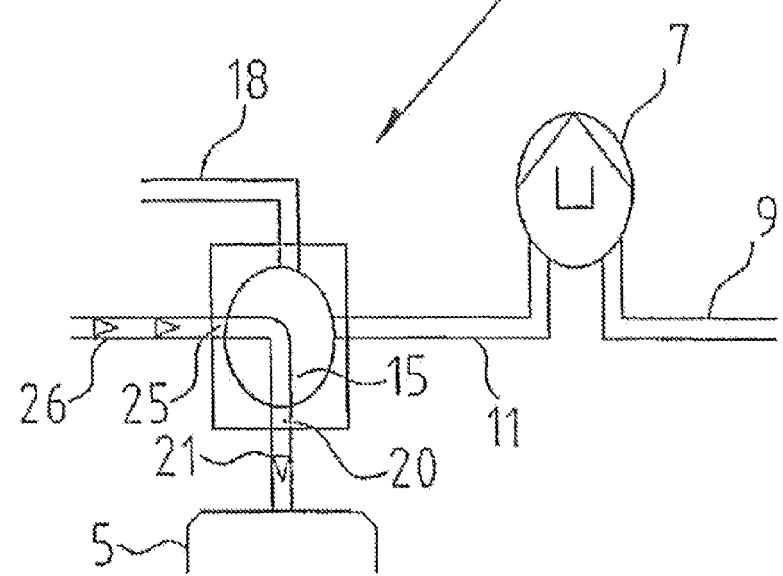

In FIG. 7(a) the sample liquid is pumped by sample pump 7 through sampling valve 12 to bypass line 18. The internal flow controller 15 is then rotated 180 degrees, as shown in FIG. 7(b), and the sample used for analysis in the liquid container in the sampling valve 12. The volume of this sample can be 0.08 ml, but can range from 0.02 ml to as much as 0.25 ml.

The sample is flushed into the reactor vessel 5 by the liquid base 4 or liquid acid 54, where appropriate, and delivered through base inlet line 26. The internal flow controller 15 is then rotated through 180 degrees to the position shown in FIG. 7(a) for reception of the next sample.

The concentration of various materials in the oxidized solution can be measured either directly or by calorimetric methods such as those outlined below.

Total Phosphate Analysis:

The total amount can be measured as phosphate by a method such as Vanadomolybdophosphoric Acid Colorimetric Method (Standard Methods for the Examination of Water and Wastewater, 20.sup.th Edition, 1998, APHA, AWWA, WEF. Method 4500-P B and C.). The principle of this method is that in Phosphate containing solutions, Ammonium Molybdate reacts in an acid medium to form a Heteropoly Acid, Molybdophosphoric Acid. The reagent used in the analysis is called Vanadate-Molybdate Reagent. In the presence of Phosphate Vanadium and Molybdenium the Vanadomolybdophosphoric Acid (yellow color) is formed. The intensity of the yellow color at 400 nm is proportional to the Phosphate concentration in the solution. Above techniques measure Total Reactive Phosphorus, Total Acid-Hydrolysable Phosphorus, Total Phosphorus (after oxidation with Ozone and Hydroxyl Radicals), and Total Organic Phosphorus.

Total Nitrogen Analysis:

The total Nitrogen in samples (oxidized with Ozone and Hydroxyl Radicals) can be measured with a UV Spectrophotometric Screening Method (Standard Methods for the Examination of Water and Wastewater, 20.sup.th Edition, 1998, APHA, AWWA, WEF. Method 4500-NO.sub.3 B.). The principle of this technique is that the absorbance of UV light at 217-220 nm is proportional to the Nitrate concentration in a solution. The oxidation with Ozone and Hydroxyl Radicals allows measuring total Nitrogen, which includes Ammonia Nitrogen, Organic Nitrogen, Nitrite, and Nitrate.

The total Nitrogen can also be measured by a Colorimetric Method. The reagent used in this method is an Acid Reagent. The principle of this technique is that the absorbance at 40 nm due to the yellow color formation between Nitrate and Acid complex is proportional to the Nitrate concentration n the solution. After oxidation with Ozone and Hydroxyl Radicals, this technique can measure Total Nitrogen including nitrogen mixed with Ammonia, Organic Nitrogen bound nitrogen concentrations, nitrate concentrations, and Nitrite.

Total Copper Analysis:

The total Copper is measured by Bathocuproine Method (Standard Methods for the Examination of Water and Wastewater, 20.sup.th Edition, 1998, APHA, AWWA, WEF. Method 3500-Cu C.). The principle of this method is that Cuprous ion forms a water-soluble orange colored chelate with Bathocuproine Disulfonate reagent. The absorbance of the color at 484 nm is proportional to the copper concentration in the solution. After oxidation with ozone and hydroxyl radicals, all liquid samples containing copper compounds can be analyzed with this method.

Total Aluminum Analysis:

The total Aluminum is measured by Erichrome Cyanine R Method (Standard Methods for the Examination of Water and Wastewater, 20.sup.th Edition, 1998, APHA, AWWA, WEF. Method 3500-A1 B.). The principle of this method is that with Erichrome Cyanine R dye, Aluminum solutions forms a red to pink complex, which exhibits maximum absorption at 535 nm. The intensity of the developed color is proportional to the Aluminum concentration in solution. After oxidation with Ozone and Hydroxyl Radicals, all liquid samples containing Aluminum compounds can be analyzed with this technique.

By applying similar standard measuring techniques, other materials such as Cobalt, Manganese, Nickel, and others can also be analyzed in the oxidized solution using the methods and apparatus of the invention.

It will be appreciated that the measurement portion of the analyzer can be adapted, as shown in FIG. 1, to provide a direct measurement of nitrogen, for example, in the sample using a photodiode array in the detector. Alternatively, the measurement portion may be adapted for the addition of a coloring reagent, as shown in FIG. 2, prior to analysis and detection of a single characteristic wavelength. Different reagents can be provided for association with different flecked materials the analyzer is requested to measure.

In the specification the terms "comprise, comprises, comprised, and comprising" or any variation thereof, and the terms "include, includes, included, and including" or any variation thereof are considered to be totally interchangeable, and they should all be afforded the widest possible interpretation.

The invention relates to an analytical method for measuring the quantity of one or more selected components in a sample generally by oxidizing a sample using hydroxyl radicals forming material in an oxidized liquid phase, then measuring that material in the oxidized liquid phase with an optical detector, with or without a reagent. Some materials may be removed or sparged from the oxidized liquid phase and measured in the gas phase by an IR detector, an ion selective electrode, or other suitable detectors.

Analysis can be made when a reagent is not used for nitrogen, phosphorus, ammonia, heavy metals, coppers, aluminum, and similar metals. One or more of these components or components similar to them can be measured simultaneously. When a reagent is used, measurements can be for one or more of phosphorus, heavy metals, coppers, aluminum, and similar metals. The measurement is performed using oxidized material in a gas or liquid phase.

The analyzer is also usable for removing inorganic material (IC), and measuring inorganic carbon, such as chalk or limestone, as an optional step. The removal of IC may take place from the main reactor 5 or from a separated IC reactor. The analyzer is also optionally usable for removal of organic material, such as methanol, acetic acid, and similar organic materials, after oxidation and measurement of the organic materials. There is also contemplated an analysis of ammonia in a liquid phase or in a gas phase.

The analyzer contemplates performing a base oxidation process, that is, measuring oxidized material in a liquid phase with an optical detector with or without reagent, like the acid process described above.

The Figures also show an ammonia gas detector, an ammonia gas removal device, a carbon dioxide removal device, a two-way base control valve, an inlet for base from the base pump, a first outlet for the liquid base to a sampling valve, a second outlet for the liquid base to the reactor vessel, and a power connection for operating the analyzer.

The invention is not limited to the embodiments hereinbefore described, but may be varied in both construction and detail within the scope of the appended claims.

What is claimed is:

1. An analyzer comprising:
   a. a reactor vessel;
   b. a sample pump for flowing a sample into the reactor vessel;
   c. a base pump connected to a base reservoir for flowing a liquid base to the reactor vessel;
   d. an ozone generator adapted to create ozone and flow the ozone to the reactor vessel;
   e. an acid pump connected to an acid reservoir for flowing a liquid acid to the reactor vessel;
   f. a sampling valve connected to the sample pump, the acid pump, and the base pump for selectively flowing the sample, the liquid base, the liquid acid, or combinations thereof, into the reactor vessel;
   g. a circulation pump connected to the reactor vessel for mixing the sample, the liquid acid, the liquid base, and the ozone to oxidize at least a portion of the sample to its lowest state forming an oxidized liquid sample;
   h. a sample chamber for receiving the oxidized liquid sample in communication with the reactor vessel;
   i. an analysis pump in communication with the sample chamber for flowing the oxidized liquid sample from the reactor vessel to the sample chamber;
   j. a reagent pump for pumping reagent from a reagent source;
   k. a mixer for introducing reagent from the reagent pump to at least one of the oxidized liquid samples;
   l. a multicomponent detector comprising at least one measuring cell for receiving the oxidized liquid sample, measuring the oxidized liquid sample optically using a frequency of absorption of at least one component in the sample; and wherein the analysis pump is reversible for flowing oxidized liquid sample into the sample chamber upstream of the measuring cell after a measurement has been made;
   m. a cleaning pump connected to a cleaning fluid reservoir for flowing a cleaning fluid to the measuring cell;
   n. a flushing pump connected to a water supply for flowing water to the measuring cell after the cleaning fluid has flowed through the measuring cell;
   o. a cleaning fluid three way valve communicating between the cleaning pump, the measuring cell and the sample chamber; and
   p. a flushing valve communicating between the flushing pump, the measuring cell, and the sample chamber.

2. The analyzer of claim 1, further comprising a second detector for optically measuring at least one frequency of absorption of at least one component in the oxidized liquid sample not measured by the first detector.

3. The analyzer of claim 1, further comprising a cleaning system for cleaning the sample pump and the sample chamber of the oxidized liquid sample, and a sample delivery line connected to the sample pump, and a sampling valve disposed in the sample delivery line.

4. The analyzer of claim 1, further comprising an ammonia gas detector connected to the reactor vessel.

5. The analyzer of claim 4, further comprising an ammonia gas removal device for removing ammonia gas from the reactor vessel.

6. The analyzer of claim 1, further comprising a flow controller connected to the ozone generator for controlling ozone production.

7. The analyzer of claim 1, further comprising an ozone destructor in communication with the reactor vessel.

8. The analyzer of claim 1, further comprising a carbon dioxide analyzer connected to the reactor vessel for detecting, measuring, or detecting and measuring inorganic carbon, organic carbon, sodium oxalates, or combinations thereof.

9. The analyzer of claim 8, further comprising a carbon dioxide removal device for removing carbon dioxide, carbonate, or combinations thereof from the reactor vessel.

10. The analyzer of claim 1, further comprising a two-way acid control valve having an inlet for receiving the liquid acid from the acid pump, a first outlet for flowing the liquid acid to the sampling valve, and a second outlet for flowing the liquid acid to the reactor vessel.

11. The analyzer of claim 1, wherein the sampling valve further comprises an internal flow controller.

12. The analyzer of claim 1, wherein the liquid acid, the liquid base, and the sample can be mixed prior to insertion in the reactor vessel for oxidization with ozone.

13. The analyzer of claim 1, wherein the multicomponent detector determines total nitrogen concentration, phosphorous concentration, phosphate concentration, ammonia concentration, concentrations of heavy metal, or combinations thereof.

14. The analyzer of claim 1, wherein the multicomponent detector is a photodiode array for optically measuring at least one component of the oxidized liquid sample.

15. The analyzer of claim 1, further comprising a processor connected to the analyzer for controlling the operations of the analyzer, reading at least one data, calculating at least one result, and displaying the at least one result on at least one display.

16. The analyzer of claim 13, wherein the total nitrogen concentration is nitrate concentrations, bound nitrogen concentrations, nitrogen mixed ammonia concentrations, nitrite concentrations, or combinations thereof.

17. The analyzer of claim 1 further comprising a ultraviolet oxidizing chamber disposed between the circulation pump and the reactor.

* * * * *